United States Patent [19]

Randell et al.

[11] 4,093,680
[45] * June 6, 1978

[54] PHOSPHORYLATED TERTIARY BUTYLATED PHENOL/PHENOL ESTER REACTION MIXTURES

[75] Inventors: Donald Richard Randell; Wilfred Pickles, both of Stockport, England

[73] Assignee: Ciba-Geigy AG, Basel, Switzerland

[*] Notice: The portion of the term of this patent subsequent to Mar. 2, 1988, has been disclaimed.

[21] Appl. No.: 696,703

[22] Filed: Jun. 16, 1976

Related U.S. Application Data

[60] Division of Ser. No. 586,756, Jun. 13, 1975, abandoned, which is a division of Ser. No. 370,455, Jun. 15, 1973, Pat. No. 3,919,158, which is a continuation-in-part of Ser. No. 74,909, Sep. 23, 1970, abandoned, which is a division of Ser. No. 645,888, Jun. 14, 1967, Pat. No. 3,576,923, said Ser. No. 645,888.

[30] Foreign Application Priority Data

Jun. 18, 1966 United Kingdom ............... 27316/66

[51] Int. Cl.$^2$ ............................................. C07F 9/12
[52] U.S. Cl. ................................................... 260/966
[58] Field of Search ......................................... 260/966

[56] References Cited

U.S. PATENT DOCUMENTS

| | | | |
|---|---|---|---|
| 2,071,323 | 2/1937 | Bass | 260/99.20 |
| 2,168,587 | 8/1939 | Shuman | 106/37 |
| 3,576,923 | 4/1971 | Randell et al. | 260/966 |

FOREIGN PATENT DOCUMENTS

450,454  7/1936  United Kingdom.

OTHER PUBLICATIONS

Buttry, "Plasticizers", 2nd ed., Cleaver–Hume Press, London, (1957), p. 39.

*Primary Examiner*—Richard L. Raymond
*Attorney, Agent, or Firm*—Wenderoth, Lind & Ponack

[57] ABSTRACT

Phosphorylated alkylated phenol/phenol ester mixtures in which the weight ratio of the alkyl moiety to the phenol moiety ranges from 0.05 to about 0.63, and the number of carbon atoms per alkyl moiety ranges from 3 to 16, preferably from 3 to 12, which mixtures have satisfactory viscosity range and impart to polymeric materials and especially to polyvinylchloride plasticized therewith good light and heat stability: a process for producing such phosphorylated alkylated phenol/-phenol ester mixtures; and polymeric materials plasticized therewith.

3 Claims, No Drawings

PHOSPHORYLATED TERTIARY BUTYLATED PHENOL/PHENOL ESTER REACTION MIXTURES

This application is a divisional of application Ser. No. 586,756, filed June 13, 1975 (now abandoned), which application in turn is a divisional of application Ser. No. 370,455, filed June 15, 1973 (now U.S. Pat. No. 3,919,158), which is in turn a continuation-in-part of application Ser. No. 74,909, filed Sept. 23, 1970 (now abandoned), which in turn is a divisional of application Ser. No. 645,888, filed June 14, 1967 (now U.S. Pat. No. 3,576,923 — U.S. Pat. No. Re. 29,540, issued Feb. 14, 1978).

DESCRIPTION OF THE INVENTION

The present invention relates to phosphorylated alkylated phenol-phenol ester mixtures, and to a process for their production.

Mixtures of triaryl phosphates have established value as plasticizers for vinyl chloride polymers. These mixtures of triaryl phosphates have hitherto been prepared by phosphorylating commercially available, pre-formed alkyl phenols, for instance mixtures comprising cresols or xylenols obtained by coal tar distillation.

The invention provides phosphorylated alkylated phenol/phenol ester mixtures wherein the weight ratio of the alkyl moiety to the phenol moiety ranges from 0.05 to 0.65 and preferably from 0.10 to 0.4 and the number of carbon atoms per alkyl moiety ranges from 3 to 16, and preferably from 3 to 12.

We have found that such novel ester mixtures when used as plasticizers have improved properties; in particular they render thermoplastic polymers into which they are incorporated outstandingly stable to light.

Furthermore, we have found that the new ester mixtures according to the invention are produced by phosphorylating, instead of the pre-formed alkyl phenols, an alkylated phenol product produced in a preliminary alkylation step from phenol.

The present invention therefore further provides, in a process for the production of improved triaryl phosphate plasticizers by phosphorylating alkylated phenols, the improvement which consists in phosphorylating an alkylated phenol product produced by contacting phenol with an alkylating agent containing from three to sixteen and preferably three to twelve carbon atoms per molecule, the proportion of alkyl moiety being within the range of from 5% to 655 and, especially in the case of alkyl moieties of up to twelve carbon atoms per molecule, 10% to 40% by weight based on the weight of the phenol moiety.

According to the present invention, a process of producing phosphate esters comprises contacting phenol with an alkylating agent and contacting the alkylated phenol product with a phosphorylating agent to produce a triaryl phosphate ester or mixture of two or more such esters, the proportion of alkyl moiety being within the range of from 5% to 65% by weight based on the weight of the phenol moiety. The present invention also comprises phospate esters when produced by this process. The invention also provides polymeric or other organic compositions comprising phosphate ester mixtures produced by this process.

The phenol stating material is advantageously phenol derived from the decomposition of cumene hydroperoxide or from the sulphonation of benzene. Preferably, the phenol is in a form free or substantially free from alkylated phenols.

The preferred alkylating agent is an olefin containing from three to sixteen and preferably three to twelve carbon atoms per molecule.

The olefin may be straight- or branched-chain or cycllic, but is preferably a mono-ene and particularly a mono-ene containing from three to eight carbon atoms, propylene, isobutylene and di-isobutylene being especially preferred. Examples of olefins which may be used as alkylating agent in the process include the following: ethylene, propylene, butene-1, butene2, isobutylene, pentene-1, 2-methyl-butenel hexene-1, cyclohexene, heptene-1, 2-methyl-pentene-1(propylene dimer), octene-1, cyclo-octene, nonene-1, cyclodecene, undecene-1, dodecene-1, cyclododecene, tetradecene and hexadecene.

The olefin may be a single olefin or a mixture of two or more thereof. Examples of mixtures which are particularly suitable for use as alkylating agents because of their ready availability include caprylene (a mixture of isomeric octenes), propylene trimer (a mixture of isomeric nonenes, propylene tetramer (a mixture of isomeric dodecenes), diisobutylene (a mixture of 2,4,4-trimethylpentene-1 and 2,4,4-trimethylpentene-2), tri-isobutylene (a mixture of dodecenes consisting predominantly of 2,4,4,6,6-pentamethylheptene-1), and tetraisobutylene (a mixture of hexadecenes consisting of predominantly of 2,4,4,6,6,8,8-heptamethylnonene-1).

In general the alkyl group introduced into the phenol molecule is an alkyl group containing the same number of carbon atoms as are present in the olefin molecule. However, if the olefin used is di-isobutylene, tri-isobutylene or tetra-isobutylene, in a proportion significantly below the proportion equimolar to the phenol with which the olefin is reacted, then the alkylated phenol product contains at least some of a tertiary alkylated phenol having a tertiarybutyl substituent in the phenolic nucleus, presumably from disproportionation of the corresponding higher tertiary-alkylated phenol with unreacted phenol.

The alkylation of the phenol may be carried out in a conventional Friedel-Crafts manner. Preferably, therefore, the alkylation is effected in the absence of a substantial amount of water. The alkylation is preferably carried out at a temperature in the range of from 15° to 250° C., a reaction temperature in the range of from 40° to 175° C. being particularly preferred, the choice of the reaction temperature employed depending on the nature of the reactants. The alkylation may be carried out at atmospheric pressure or at an elevated pressure.

The alkylation of the phenol is conveniently effected in the presence of an alkylation catalyst, which is preferably a Lewis acid or a Bronsted acid. Examples of Lewis acids which may be used include aluminium chloride, ferric chloride, stannic chloride, zinc chloride, boron trifluoride and complexes thereof, and titanium tetrachloride. Examples of Bronsted acids which may be used include sulphuric acid, orthophosphoric acid, p-toluene sulphonic acid, perchloric acid, sulphonated polystyrene resins or other acid forms of ion-exchange resins and acid-treated montmorillonite and other activated clays and earths. The proportion of catalyst present is preferably in the range of from 0.001% to 10% by weight, and especially from 0.05% to 5% by weight, based on the weight of the phenol present in the reaction mixture.

The alkylation is preferably carried out in the presence of gaseous hydrogen halide, particularly if a Lewis acid is used as alkylation catalyst. For instance, if the catalyst is aluminum chloride, the alkylation is preferably effected in the presence of hydrogen chloride which may be added to the reaction mixture or may be formed by decomposition of some of the aluminium chloride catalyst.

The preparation of alkyl moiety to phenol moiety is within the range of from 5% to 65% by weight. If this proportion is below 5%, the amount of unreacted phenol in the alkylation product, after phosphorylation, is found to be sufficient to cause the formation of relatively large quantities of the solid triphenyl phosphate in the phosphate ester product, and the presence of this solid material is unacceptable if the ester is to be used as a plasticiser or other purpose where a homogeneous ester or ester mixture is required. If the proportion of alkyl moiety to phenol moiety is substantially above 65%, the resulting phosphate ester produced is found to have too high a viscosity and boiling range to enable it to be readily purified or used as a plasticiser for vinyl chloride polymers or copolymers, and the ester may have the further disadvantage of being incompletely compatible with the polymeric material.

Preferred proportions of alkyl moiety to phenol moiety are within the range of from 7% to 50% by weight of alkyl moiety based on the weight of the phenol, a proportion within the range of from 10% to 40% by weight being especially preferred, as the phosphate esters produced from these proportions have especially good plasticising properties when incorporated into polyvinyl chloride. In particular, the phosphate esters produced from these proportions render polyvinyl chloride into which they are incorporated as plasticisers outstandingly stable to light.

The process of the invention may conveniently be carried out by reacting substantially the whole of the product resulting from the alkylation of the phenol with the alkylating agent with the phosphorylating agent to produce the alkylated phenol phosphate ester or esters. The alkylated phenol product from the alkylation stage is preferably used directly as starting material in the phosphorylation stage, if desired with the addition of further phenol or with the addition of further alkylated phenol which has already been prepared by the alkylation process, provided that the alkylated phenel/phenol mixture which is phosphorylated contains from 5% to 65% by weight of alkyl moiety based on the weight of phenol moiety.

The crude product of the phenol alkylation may also be freed from part or all of any alkylation catalyst present: part or all of the catalyst may advantageously be removed if it would interfere with the course of the subsequent phosphorylation reaction, and replaced with another Lewis acid in order, for example to prevent catalyst deactivation or contamination or to provide a more effective catalyst for the phosphorylation reaction.

If it is desired to use the same catalyst for both the alkylation and phosphorylation stages, a particularly preferred catalyst is aluminium chloride.

The phosphorylation of the alkylated phenol product, produced by the reaction of the phenol with the alkylating agent, may be carried out under a wide range of conventional phosphorylation reaction conditions. If the reaction is effected in the presence of a Lewis acid catalyst, this may be different from, but is preferably the same as, the catalyst used in the alkylation stage. The preferred phosphorylation catalyst is, however, aluminium chloride. The proportion of catalyst present is preferably in the range of from 0.001% to 5% by weight, and especially from 0.05% to 1% by weight based on the weight of the phenol present in the alkylated phenol product reacted with the phosphorylating agent. The preferred phosphorylating agent is phosphorus oxychloride, but phosphorus oxybromide or phosphoric acid may also be employed.

The phosphorylation is preferably carried our at a temperature in the range of from 15° to 250° C., a reaction temperature in the range of from 100° to 225° C. being particularly preferred in order to obviate the use of larger proportions of phosphorylating agent with respect to the alkylated phenol which may be necessary to secure good yields of the desired phosphate ester when operating the reaction at lower temperatures.

The proportion of the phosphorylating agent to that of the alkylated phenol may be varied within a wide range, depending on the nature of the reactants and the rection conditions, but is preferably within the range of from 1 to 5 moles, and particularly within the range of from 2.5 to 3.5 moles, of alkylated phenol per mole of phosphorylating agent.

The alkylated phenol phosphates produced in accordance with the present invention are valuable in a wide variety of uses. For instance, they find application as plasticisers or other additives to vinyl chloride polymers and co-polymers, polyolefins, cellulose esters, or other synthetic polymers; in the formulation of hydraulic or other functional fluids; as ignition control or other additives for fuels, and as extreme pressure additives or other additives to lubricants. Furthermore, the phosphate esters produced in accordance with the present invention have satisfactory toxicological preparation as compared with phosphate esters produced by processes already in commercial use.

It is an advantage of the process of the present invention that, by controlling the addition of the alkylating agent to the phenol, the proportion alkyl groups in the alkylated phenol thus obtained can be adjusted to provide, after the subsequent phosphorylation stage has been carried out, a phosphate ester product which is especially suited to any particular desired application.

The present invention provides a process which is particularly suited to the production of phosphate esters or ester mixtures, which have optimal usefulness as a plasticiser for vinyl chloride polymers or co-polymers, the proportion of alkyl groups present in the plasticizer ester or ester mixture being within certain limits, which depend on the nature of the composition plasticized. The degree of alkylation required is readily achieved by controlling the addition of the alkylating agent to the phenol within the above-stated limits.

The present invention also provides compositions of organic materials comprising a functionally effective proportion of a phosphate ester produced by a process of the invention. The composition may, for example, comprise synthetic polymer, in particular vinyl chloride polymers and a plasticising proportion of the ester.

The following Examples further illustrate the present invention. Parts by weight shown therein bear the same relation to parts by volume as do kilograms to liters. Parts and percentages are expressed by weight unless otherwise stated.

EXAMPLE 1

940 parts of phenol were placed in a reactor and fitted with a stirrer, gas inlet tube, thermometer and reflux condenser. After heating the reactor at 50° C., 44.5 parts of anhydrous aluminium chloride were added. Isobutylene was then passed in, while stirring the reaction mixture vigorously, until 71 parts of isobutylene had been absorbed. During the addition of the isobutylene, the temperature of the reactor contents was maintained at 50° C. by external cooling.

The reaction product, comprising 81.2% phenol and 18.8% p-tertiarybutyl-phenol, was cooled to 15° C. and 537.0 parts of phosphorus oxychloride were added over 45 minutes while maintaining the reaction mixture at 50° C. The resulting mixture was gradually heated to 150° C. over 4 hours and was then maintained at 150° C. for a further period of 4 hours.

To the resulting product, after cooling, were added 1500 parts by volume of toluene and the mixture was washed with a mixture of 100 parts by volume of concentrated hydrochloric acid and 2000 parts by volume of water for 30 minutes at 60° C. and then with a mixture of 50 parts by volume of concentrated hydrochloric acid and 2000 parts by volume of water for 10 minutes at 60° C. This acid washing was then followed by a five-fold washing with 2,000 parts by volume of water for 10 minutes at 60° C. The toluene present was then distilled off and the product subjected to fractional distillation.

The fraction distilling over at boiling range 218° to 256° C. at 0.7 millimeter of mercury pressure, amounting to 998 parts, was collected. The fraction was washed, firstly, with a mixture of 30 parts 46% sodium hydroxide solution and 1335 parts of water for 3 hours at 40°C. and, secondly, with a mixture of 15 parts of 46% sodium hydroxide solution and 1335 parts of water for 1 hour at 40° C. This alkali wash was then followed by washing twice with 2000 parts of water for 30 minutes at 40° C. to remove any sodium hydroxide present. The resulting product was dried by heating at 95° to 100° C. at 12 to 15 millimeters of mercury pressure.

The phosphate ester produced was an almost colourless oily liquid consisting of a mixture of triphenyl phosphate, tri-p-tertiarybutyl-phenyl phosphate and mixed phosphates derived from both phenol and p-tertiarybutyl-phenol in various proportions, and had an acid value of less than 0.1. (In all the Examples in this Specification, acid values are expressed as milligrams hydroxyl per gram).

EXAMPLE 2

The procedure described in Example 1 was carried out except that the passage of isobutylene into the heated reactor was continued until 176 parts had been absorbed, the proportions of reactants and the reaction and recovery conditions being otherwise essentially the same.

The reaction product from the alkylation of the phenol with the isobutylene consisted of 57.7% phenol and 42.3% p-tertiarybutyl-phenol. The phosphate ester produced was an almost colourless oily liquid, having boiling range 196° to 250° C. at 10.3 millimeter of mercury pressure, amounting to 1131 parts and having acid value 0.2. The ester product consisted essentially of triphenyl phosphate, tri-p-tertiarybutyl-phenyl phosphate and mixed phosphates derived from both phenol and p-tertiarybutyl-phenol in various proportions.

EXAMPLE 3

The procedure described in Example 1 was carried out except that propylene was used as alkylating agent instead of isobutylene, the propylene being passed into the heated reactor containing the phenol and aluminium chloride until 168 parts had been absorbed. The proportions of reactants and the reaction and recovery conditions were otherwise essentially the same.

The reaction product from the alkylation of the phenol with the propylene consisted of unreacted phenol and isopropylated phenol. The phosphate ester produced was an almost colourless oily liquid having boiling range 185° to 210° C. at 1 to 1.5 millimeter of mercury pressure, amounting to 1100 parts and having acid value 0.19. The ester product consisted of triphenyl phosphate, tri-isopropyl-phenyl phosphate and mixed phosphates derived from both phenol and isopropyl phenol in various proportions.

In order to demonstrate the superior properties of the phosphate esters produced by the procedures described in Examples 1 to 5 over phosphate esters produced by similarly phosphorylating commercially available preformed alkylated phenols instead of the alkylated phenol produced as a first stage in these Examples, the following comparative Examples A to D are given followed by a description of the comparative tests made on the seven phosphate ester products in plasticising polyvinyl chloride film.

Samples of each of the phosphate esters produced by Examples 1 to 3 were formulated into polyvinyl film in a conventional manner, the composition in each case being 65 parts "Breon 111" polyvinyl chloride
35 parts phosphate ester under test
3 parts "Ferroclere 1820" stabiliser The film samples were then tested for stability to heat and light.

The heat stability tests were conducted in an oven heated at 180° C. The results showed that the polyvinyl chloride containing the phosphate esters of the present invention had the same good stability to heat as did the samples containing the phosphate esters made by the conventional procedures described in Comparative Examples A to D.

The light stability tests were carried out by exposing pressed samples of the same polyvnyl chloride formulations used in the heat stability tests having a thickness of 0.05 inch, to a "Xenotest" lamp. Even after 600 hours exposure, the film samples containing, as plasticisers, the phosphate esters produced by the procedures Examples 1 to 3 showed no significant detectable change in colour, whereas film samples containing plasticiser phosphate esters produced by known procedures from commercially available cresol or xylenol mixtures obtained from coal tar distillation exhibited marked yellowing.

EXAMPLE 4

282 parts of phenol and 13.3 parts of anhydrous aluminium chloride were placed in a reactor and the temperature of the reactor contents was raised to 120° C. Propylene was then passed into the mixture over a period of 1½ hours, after which time the uptake of propylene was 42 parts (equivalent to 1 mole per 3 moles of phenol). The reaction mixture was then cooled to 15° C. and 161.4 parts of phosphorus oxychloride, representing 5% excess over the equimolar proportion of phenol, were added over 30 minutes while maintaining the reactor at 15° C. The reaction mixture was then heated to 150° C. over 4 hours and then maintained at the same temperature for a further period of 4 hours, during which hydrogen chloride gas was evolved.

To the resulting product, after cooling, were added 250 parts of toluene and the mixture was washed with aqueous hydrochloric acid at 60° C. and then with water. The toluene and any traces of water were then removed by distillation at 0.2 millimeters of mercury pressure.

The fraction distilling off at boiling range 190° to 238° C. was collected and washed with aqueous sodium hydroxide solution and with water at 40° C. Traces of water were removed by distillation ar 12 to 15 millimeters of mercury pressure. The phosphate ester produced, consisting of triphenyl phosphate and isopropylated phenyl phosphates, was treated with activated carbon and finally filtered.

In this way, 290.4 part of the purified product were obtained, representing a yield of 78.5% based on the amount of propylene passed into the reactor. The product had an acid value of 0.07.

EXAMPLE 5

The procedure described in Example 4 was carried cut using 63 parts of propylene, which were passed into the reactor at 120° C. for 2.75 hours, the proportions and reaction and recovery conditions being otherwise essentially the same.

The product had boiling range 175° to 206° C at 1 millimeter of mercury pressure, 336.7 parts being obtained representing a yield of 87%. The ester obtained, which consisted of a mixture of triphenyl phosphate and isopropylated-phenyl phosphates, had an acid value of 0.08.

EXAMPLE 6

The procedure described in Example 4 was carried out using 84 parts of propylene passed into the reactor over 3½ hours, the proportions and reaction and recovery conditions being otherwise essentially the same.

336 parts of the purified phosphate ester product were obtained, representing a yield of 79.6% and consisting of a mixture of triphenyl phosphate and isopropylated-phenyl phosphates. The product had an acid value of 0.01.

EXAMPLES 7 TO 9

The procedure described in Example 4 was carried out, except that the quantities of isobutylene shown in Table 1 were passed into the mixture of phenol and aluminium chloride instead of the propylene there used during the stated periods, the properties and reaction and recovery conditions being otherwise essentially the same.

The boiling ranges and amounts of the purified phosphate esters obtained, in each case consisting essentially of a mixture of triphenyl phosphate, tri-p-tertiarybutyl-phenyl phosphate and mixed phosphates containing both phenol and p-tertiarybutyl-phenol in various proportions are shown in Table I.

TABLE 1

| Example | 7 | 8 | 9 |
|---|---|---|---|
| Parts isobutylene introduced: | 33.7 | 42.1 | 50.5 |
| Passed in for (minutes): | 25 | 35 | 50 |

TABLE 1-continued

| Example | 7 | 8 | 9 |
|---|---|---|---|
| Boiling Range: | 185° to 218° C. (0.1 millimeter) | 200° to 235° C. (0.6 millimeter) | 216° to 252° C. (1 millimeter) |
| Parts ester obtained: | 257.8 | 292.5 | 332.8 |

EXAMPLES 10 TO 13

The procedure described in Example 4 was carried out, except that isobutylene was passed into the mixture of phenol and aluminium chloride instead of the propylene there used, the temperature of the reactor contents being maintained at 50° C. during the alkylation instead of at 120° C. The proportions and reaction and recovery conditions were otherwise essentially the same.

The boiling ranges and properties of the purified phosphate esters thus produced, in each case consisting essentially of a mixture of triphenyl phosphate and tertiarybutylated-phenyl phosphates, were essentially the same as those in Examples 7 to 9.

EXAMPLES 14 TO 16

The procedure described in Example 4 was carried out except that di-isobutylene (a mixture consisting of 75% 2,4,4-trimethylpentene-1 and 25% 2,4,4-trimethylpentene-2) was used as alkylating agent instead of the propylene there used, the quantities of di-isobutylene introduced into the mixture of phenol and aluminium chloride being shown in Table 2 and the proportions and reaction and recovery conditions being otherwise essentially the same.

The purified phosphate esters thus produced, in each case comprised triphenyl phosphate, tri-p-tertiarybutyl-phenyl phosphate and mixed phosphates containing both phenol and p-tertiarybutyl-phenol in various proportions.

TABLE 2

| Example | 14 | 15 | 16 |
|---|---|---|---|
| Parts di-isobutylene introduced: | 33.6 | 42.0 | 50.4 |
| Parts ester obtained: | 297.6 | 353.5 | 330.0 |

The analysis of the hydrolysate from the phosphate ester did not reveal the presence of any octylated phenol which might have been expected from the use of an octane as alkylating agent, indicating complete disproportionation to the tertiarybutyl analogue.

As a comparison with Examples 14 to 16 of the invention, the same procedure was attempted in two separate runs except that the amounts of di-isobutylene introduced into the mixture of phenol and aluminium chloride in the reactor were 6.8 parts and 3.4 parts, representing proportions of alkylating agent based on the weight of phenol in the reactor of approximately 2.4% and 3.0% (compared with the equivalent figures of 12.0%, 15.0% and 10.0% respectively for the preparations used in Examples 14, 15 and 16), and which are thus not embodiments of the present invention.

On reaching the step of removing toluene and traces of water from the phosphorylated product, solid triphenyl phosphate precipitated out, so that a homogeneous ester product could not be produced.

EXAMPLE 17

This Example illustrates the use of phosphate esters produced by the process of the present invention as plasticizers for cellulose triacetate film.

A solution of celluose triacetate in a solvent mixture comprising 90 parts by volume methylene chloride and 10 parts by volume methanol was prepared by dissolving 50 parts cellulose triacetate (acetyl content 62.5%, expressed as acetic acid) in 350 parts of the solvent mixture. To this was added 10 parts of plasticiser, and the container was rotated on a tumbler for 24 hours to mix the components thoroughly. The solution was allowed to stand until all air bubbles were released and then cast on a strip of aluminium foil using a doctor blade adjusted to give a film thickness of 0.05 millimeter when dry. The films, when dry, were removed from the aluminium foil and stored at a constant temperature of 23° C. and 50% relative humidity for seven days before testing.

A range of phosphate esters prepared from phenol alkylated with isobutylene or propylene as described in Examples 1, 2 and 3 were used as plasticisers as shown in Table 3, triphenyl phosphate being also included to give comparative data. In all cases dry, clean, flexible films were obtained which showed no change on storage for two months at 23° C. and 50% relative humidity.

Tensile strength determinations were carried out on portions of these films at 23° C. and 50% relative humidity using 3 inch long dumbell-shaped specimens cut from the film using a sharp knife-edged punch. Testing was carried out at a rate of extension of 0.25 inch per minute, the tensile strength being calculated from the maximum load recorded and the initial area of cross-section. Eleven specimens were tested for each film and the value quoted in Table 3 for the respective compositions in the arithmetic mean of these results. The plasticiser content in each case was 20% expressed by weight based on the weight of the cellulose triacetate.

TABLE 3

|  | Tensile strength (Kg/mm$^2$) |
| --- | --- |
| Triphenyl phosphate | 5.45 |
| Alkylated phenol phosphate as prepared in Example 1 | 6.24 |
| Alkylated phenol phosphate as prepared in Example 2 | 6.29 |
| Alkylated phenol phosphate as prepared in Example 3 | 6.50 |

These results demonstrate the improved plasticizing properties of the phosphate esters produced by the process of the present invention as compared with triphenyl phosphate, which is the conventional cellulose triacetate plasticser.

EXAMPLE 18

The following Example illustrates the use of the esters of the present invention in hydraulic fluid compositions.

Phosphate esters produced by the processes described in Examples 1 and 3 were found to possess properties rendering them valuable base-stocks in formulating industrial fire-resistant hydraulic fluids; in particular the esters have been found to have high flash points, fire points and autogeneous ignition temperature.

Other desirable requisites for hydraulic fluids which the esters possess include superior viscosity/temperature properties, low pour points and little tendency to crystallise at low temperatures.

These properties are shown in Table 4. Viscosity determinations, pour points, flash points and fire points were carried out by the methods described in "Institute of Petroleum Standards for Petroleum and its Products," Part 1; autogeneous ignition temperatures and Viscosity Indices by methods described in "Book of ASTM Standards," Part 17. A.S.T.M. slopes were obtained from tables prepared from A.S.T.M. Viscosity-temperature charts. Low temperature storage tests consisted of maintaining samples of the fluids, in sealed glass tubes, for seven days at each of a series of gradually decreasing temperatures.

TABLE 4

|  | Phosphate ester prepared by Example 2 | Phosphate ester prepared by Example 3 |
| --- | --- | --- |
| Viscosity at 210° F (contistokes) | 4.91 | 3.77 |
| Viscosity at 100° F (centistokes) | 36.84 | 22.76 |
| Viscosity Index (210° to 100° F.) | 35.4 | 26.4 |
| A.S.T.M. Slope (210° to 100° F.) | 0.829 | 0.837 |
| Flash point (° F.) | 475 | 460 |
| Fire point (° F.) | 605 | 590 |
| Autogeneous ignition temp. (° F.) | 1130 | 1177 |
| Pour point (° F.) | −10 | −25 |
| Low temperature storage | No cloud or crystals at temperatures down to −32° C. | |

EXAMPLE 19

The following Example illustrates the use of the esters of the present invention as extreme pressure additives for lubricating oils.

Phosphate esters produced by the processes described in Examples 1 and 3, when added in small quantities to lubricating oils (which can be naturally occurring or synthetic), have been shown to provide increased load-carrying and anti-wear properties. In other words they are useful as mild extreme-pressure/anti-wear additives.

The well-known Shell 4-Ball Lubricant Testing Apparatus was used to measure the Mean Hertz Load and Incipient Seizure Load of a paraffin oil (Shell Talpa 20) (viscosity 88 centistokes at 100° F.) with and without the addition of the phosphates of the invention. This apparatus consists essentially of a half-inch diameter steel ball which is rotated at a speed of 1,420 revolutions per minute in contact with three similar balls held stationary in a test cup, by means of a clamping ring and nut, and immersed in the oil under test. A lever system exerts a known, variable force (applied load) between the stationary ball and the rotating ball. During the test small circular scars are worn on each of the fixed balls and the size of these scars gives an indication of the anti-wear and load carrying properties of the lubricant.

The Mean Hertz Load is obtained from a series of test runs carried out at twenty different specified loadings and is the average of these loads corrected for the difference between the actual diameters of the wear scars formed and the Hertz diameter which is the area of contact between the balls under static load. The Incipient Seizure Load is the applied load at which the oil film first breaks down, with a rapid increase in friction and wear resulting. The oil-film can subsequently reform at this stage.

TABLE 5

| Additive used | Concentration | Mean Hertz Load | Incipient Seizure Load (% g) |
|---|---|---|---|
| None | — | 19.6 | 45–48 |
| Phosphate prepared by Example 1 | 2% w/w | 27.2 | 60–63 |
| Phosphate prepared by Example 3 | 2% w/w | 23.6 | 55–57 |

The results obtained from tests carried out on the alkylated henol phosphates prepared by Examples 1 and 3 are shown in Table 5. These clearly indicate the beneficial effect of adding the phosphate esters to the oil.

EXAMPLE 20

The following Example illustrates the use of the esters of the present invention as plasticisers in tiles made of vinyl polymers or copolymers which are fixed to the surface to be tiled with bituminous adhesives.

It is already well known that if vinyl tiles containing certain types of plasticiser are affixed with bituminous adhesives, the plasticiser may diffuse out of the polymer, and cause the adhesive to soften and flow out between the tiles. If the softened adhesive reaches the decorative surfaces of the tiles, they may be spoiled by being stained with the softened adhesive. Accordingly tests have been devised to measure the ability of a plasticiser not to migrate into bituminous adhesive, for instance the "asphalt leaching test". In this test, paper strips, coated on one side with bitumen, are immersed in the plasticiser and the colour change of the plasticiser is determined after immersion of the bitumen-coated paper for one hour.

This test was carried out upon a sample of a phosphate ester prepared in according with Example 3 except that sulphuric acid-activated fullers' earth was used as catalyst in the alkylation stage instead of the aluminium chloride there used. The initial colour, as measured on the Lovibond comparitor, was 0.5 yellow, 0.0 red, and the final colour was 1.2 yellow, 0.1 red. As a comparision, the same test was carried out on a sample of phosphate estor produced as described in Comparative Example C, the initial colour of this trixylenyl phosphate was 0.57 yellow, 0.0 red and the final colour was 6.0 yellow, 1.0 red.

This comparison illustrates, therefore, the slight colour change of 0.7 yellow, 0.1 red produced by the phosphate ester of the present invention, as against the very marked colour change of 5.5 yellow 1.0 red produced by a typical phosphate ester of the prior art, and signifies that the phosphate ester of the invention would have especial and unexpectedly great value as a plasticiser for vinyl polymer tiles to be fixed with a bituminous adhesive.

EXAMPLE 21

940 parts of phenol were placed in a reactor fitted with stirrer, gas inlet tube, thermometer and reflux condenser. The phenol was melted and 75 parts of "Fulmont 237" activated montmorillonite (The Fullers' Earth Union Ltd., Redhill, Surrey) were added. The reactor was now heated to 105° to 110° C. and propylene was passed in, while stirring the mixture vigorously until 240 parts of propylene had been adsorbed. During the addition of the propylene the temperature of the reactor was maintained at 105° to 110° C. The reaction mixture was allowed to cool and the montmorillonite was removed by filtration. The reaction product was found by gas/liquid chromatographic analysis to have the following percentage composition:

phenol — 41.7
mono-isopropylphenois — 44.3
di-isopropylphenois— 10.9
tri-isopropylphenols — 1.6
ethers — 1.3
unknown — 0.2

By repeating this procedure, except that the amount of the montmorillonite was reduced to 18.8 parts, the proportion of the ether reactants remaining unchanged, an isopropylated phenol product having a substantially identical percentage composition was obtained.

44.5 parts of anhydrous aluminium chloride were added, followed by the addition of 537 parts of phosphorous oxychloride over a period of 45 minutes while maintaining the reaction mixture at 50° C. The recovery procedure described in Example 1 was then followed. The fraction distilling over the boiling range 200 – 220° C. at 0.5 millimeter of mercury pressure, amounting to 1158 parts, was collected. This fraction was washed and dried as described in Example 1.

The phosphate ester produced was an almost colourless oil consisting of a mixture of triphenyl phosphate, and mixed phosphates derived from both phenol and isopropylated phenols in various proportions, and had an acid value of 0.1.

EXAMPLES 22 TO 27

The phosphate ester produced by the procedure described in Example 21 was subjected to a standard testing to determine its liquid physical properties and to evaluate its plasticising properties (Example 22). A sample of the ester, and of the two other phosphate esters (Examples 23 and 24) produced by the procedure of Example 21, except that the amounts of propylene used in the alkylation stage had the values given in Table 6 instead of the 240 parts in the procedure of Example 21, and of three other phosphates (Examples 25 to 27) produced by the procedures described in Examples 7, 8 and 14 respectively, were each formulated into polyvinyl film in a conventional manner, the composition in each case being 65 parts polyvinyl chloride ("Breon 111")
35 parts phosphate ester under test
4 parts white lead paste
1 part calcium stearate The results of the determination of liquid physical properties and evaluation of plasticising properties are shown in Table 6. These results illustrate the value of the phosphate esters of the present invention as plasticisers of polyvinyl chloride.

TABLE 6

| Example | 22 | 23 | 24 | 25 | 26 | 27 |
|---|---|---|---|---|---|---|
| Alkylating agent | propylene | propylene | propylene | iso-butylene | iso-butylene | di-iso-butylene |
| Parts: Agent | 240 | 105 | 340 | 33.7 | 42.1 | 33.6 |
| Parts: Phenol | 940 | 940 | 940 | 282 | 232 | 282 |
| Viscosity (centistokes at 25° C.) | 77.6 | 42.8 | 155.4 | 54.3 | 62.7 | 43.5 |
| Density (gm/ml.at 25° C.) | 1.144 | 1.181 | 1.119 | 1.178 | 1.170 | 1.188 |
| Refractive Index at 25° C. | 1.5481 | 1.5553 | 1.5423 | 1.5564 | 1.5551 | 1.5662 |
| Hazen number | 75 | 100 | 200 | 75 | 50 | 60 |
| I.R.H.D. (hardness) | 88 | 81 | 94.8 | 88.7 | 90.5 | 87.8 |

TABLE 6—continued

| Example | 22 | 23 | 24 | 25 | 26 | 27 |
|---|---|---|---|---|---|---|
| $T_3$ (° C.) Clash & Berg (° C.) | +10 +3 | +6 0 | +13 +5 | +12.5 +7.5 | +14.6 +8.5 | +9 +6 |
| Volatility | 0.91 | 2.0 | 0.8 | 1.38 | 1.09 | — |
| Compond Volume | 1.3 | 3.8 | 2.4 | 5.73 | 1.08 | 1.2 |
| resistivity (ohm.cm.) | $\times 10^{13}$ | $\times 10^{12}$ | $\times 10^{13}$ | $\times 10^{13}$ | $\times 10^{14}$ | $\times 10^{13}$ |
| Extractions (%) | | | | | | |
| Water | +0.06 | 0.17 | +0.32 | +0.05 | 0 | 0.4 |
| Soap | 10.4 | 13.3 | 8.5 | 10.1 | 9.0 | 11.8 |
| Detergent | 7.4 | 13.5 | 5.6 | 10.3 | 9.0 | 12.5 |
| Mineral Oil | 12.5 | 14.0 | 9.3 | 10.1 | 8.0 | 10.6 |
| Olive Oil | 12.6 | 14.0 | 8.9 | 10.8 | 8.6 | 10.5 |
| Petrol | 14.9 | 15.0 | 16.6 | 17.4 | 18.0 | 18.2 |

The $T_3$ figure given is the temperature in degrees Centigrade at which the material has a modulus of rigidity of 1000 kilograms per square centimetre; it is a low-temperature stiffness figure.

The I.R.H.D. figure in the International Rubber Hardness Degrees.

The volatility is given as the percentage weight loss from a 15 × 1 × 0.1 centimeter specimen in 96 hours at 82.5° C. in a forced draught air oven. The extractions are given as percentage weight loss from a thin sheet (3 × 3 × 0.007 inch) immersed under the following conditions.

| Petrol | 75% iso-octane; 25% toluene 1 hour at 23° C. |
|---|---|
| Mineral Oil | Oil to specification D.E.F. 2001; 24 hours at 60° C. |
| Olive Oil | B.P. quality; 24 hours at 60° C. |
| 1% Soap | 1% solution of soap flakes in distilled water; 24 hours at 60° C. |
| 1% detergent | 1% solution of triethanolamine lauryl sulphase in distilled water; 24 hours at 60° C. |
| Distilled water | 24 hours at 60° C. |

EXAMPLE 28

940 parts of phenol were placed in a reactor fitted with stirrer, dropping funnel, thermometer and reflux condenser. 10 parts of concentrated sulphuric acid were added and the reactor was heated to 100° C. 280 parts of caprylene were added dropwise over a period of 1 hour and the reaction mass was then maintained at 100° to 105° C. for a further 4 hours. The excess sulphuric acid was neutralised by stirring the reaction mixture with 11 parts of solid sodium carbonate at 100° to 105° C. for 2 hours and the solid was removed by filtration after cooling. To the filtrate, which was 1124 parts of a mixture of phenol and capryl phenols, was added 41 parts of anhydrous aluminium chloride, followed by 495 parts of phosphorus oxychloride added over a period of 45 minutes while maintaining the reaction mixture at 50° C. The recovery procedure described in Example 1 was then followed.

The ester product, consisting of triphenyl phosphate and mixed phosphates derived from both phenol and capryl phenols, was a pale yellow oil boiling over the range 168° to 280° C. at 0.2 millimeter of mercury pressure. It had acid value 0.2 and amounted to 1092 parts.

EXAMPLE 29

376 parts of phenol were placed in a reactor fitted with stirrer, dropping funnel, thermometer and reflux condenser. 0.06 parts of perchloric acid (specific gravity 1.70) were added and the mixture heated to 45° C. 109 parts of cyclohexene were added dropwise over a period of 1 hour maintaining the reaction temperature at 45° C. The mixture was stirred at 45° C. for a further 1 hour, and then unreacted cyclohexene (amounting to 17 parts) was removed by distillation at 12 millimeters of mercury pressure.

17 parts of anhydrous aluminium chloride were added, followed by 215 parts of phosphorus oxychloride, added over a period of 45 minutes while maintaining the reaction mixture at 50° C. The resulting mixture was gradually heated to 150° C. over 4 hours and was then maintained at 150° C. for a further period of 4 hours.

To the resulting product, after cooling, were added 600 parts by volume of toluene and the mixture was washed with a mixture of 40 parts by volume of concentrated hydrochloric acid and 800 parts by volume of water for 30 minutes at 60° C. and then with a mixture of 20 parts by volume of concentrated hydrochloric acid and 800 parts by volume of water for 10 minutes at 60° C. This acid washing was then followed by a five-fold washing with 800 parts by volume of water for 10 minutes at 60° C. The toluene present was then removed by distillation and the product subjected to fractional distillation.

The fraction distilling over at boiling range 182° to 250° C. at 0.1 millimeter of mercury pressure, amounting to 388 parts, was collected. The fraction was washed, firstly, with a mixture of 12 parts 46% sodium hydroxide solution and 530 parts of water for 3 hours at 40° C. and, secondly, with a mixture of 6 parts of 46% sodium hydroxide solution and 530 parts of water for 1 hour at 40° C. This alkali wash was then followed by washing twice with 800 parts of water for 30 minutes at 40° C. to remove any sodium hydroxide present. The resulting product was dried by heating at 95° to 100° C. at 12 to 15 millimeters of mercury pressure.

The phosphate ester produced was pale yellow, oily liquid consisting of a mixture of triphenyl phosphate, and mixed phosphates derived from both phenol and cyclohexyl phenols, and had an acid value of less than 0.1.

EXAMPLE 30

Four samples of a PVC compound were plasticised with different plasticisers by milling for 15 minutes at 165° C. and pressing the resultant hide in a press to give 0.050 inch clear sheets, the composition being:
100 parts PVC sold under the mane Polyer Corvic D65/02
50 parts plasticiser
2 parts Irgastab BC.206
0.5 parts stearic acid
The plasticisers in each case were:
(1) trixylyl phosphate
(2) tritolyl phosphate
(3) a tertiary butyl phenyl phenyl phosphate in which the butylated phenol from which the phosphate is prepared is obtained by alkylating with 14.9% isobutylene based on the weight of the phenol with which it is contacted, and
(4) a tertiary butyl phenyl phenyl phosphate in which the butylated phenol from which the phosphate is prepared is obtained by alkylating with 11.9% isobutylene based on the weight of the phenol with which it is contacted.

Samples of the four sheets were then exposed in an accelerated weathering apparatus for 436 hours. On inspection, it was apparent that whereas all the sheets had developed a yellow colouration, those containing tertiary butyl phosphate were a much paler colour than those containing trixylyl phosphate and tritolyl phosphate.

EXAMPLE 31

This Example illustrates the improvement in clear point in PVC of the plasticisers of this invention over non-phosphate plasticisers.

8 samples of a dilute suspension of PVC in plasticiser was heated slowly at a rate of 2° C. per minute and observing the changes that take place through a microscope. The temperature at which the PVC particle swollen with plasticiser becomes indistinguishable from the continuous phase is recorded as the clear point. The lower the clear point the more rapidly will the plasticiser gel the PVC under normal processing conditions.

The plasticisers used were as follows:

Five triaryl phosphate mixtures prepared by contacting phenol with:
(1) 9.5%
(2) 10.7%
(3) 11.9%
(4) 13.1%
(5) 14.9%
by weight of isobutylene based on the total weight of phenol and afterwards phospherylating:
(6) Dioctyl phthalate
(7) Dioctyl adipate
(8) Polymeric plasticiser (polybutylene adipate polyester)

The results are shown in Table 7.

TABLE 7

| Plasticiser | Clear Point ° C. |
|---|---|
| 1 | 79 |
| 2 | 78 |
| 3 | 83 |
| 4 | 85 |
| 5 | 88 |
| 6 | 115 |
| 7 | 138 |
| 8 | 155 |

We claim:

1. A phosphate ester composition consisting essentially of a phosphorylated tertiary butylated phenol/phenol ester mixture wherein the weight ratio of the tertiary butyl moiety to phenol moiety ranges from 0.10 to about 0.4, which ester is prepared by steps comprising:
    (a) alkylating at a temperature of about 15° to 250° C in the presence of a Lewis acid or a Bronsted acid as a catalyst, phenol with isobutylene or diisobutylene to obtain a tertiary butylated phenol reaction mixture, and
    (b) reacting said tertiary butylated phenol reaction mixture with a phosphorylating agent.

2. A composition according to claim 1 wherein at least part of the alkylation catalyst is removed from the alkylation reaction mixture prior to phosphorylation.

3. A composition according to claim 1 wherein the phosphorylating agent is selected from the group consisting of phosphorus oxychloride, phosphorus oxybromide and phosphoric acid and step (b) is conducted at 15° to 250° C in the presence of a Lewis acid.

* * * * *